United States Patent [19]

Dann et al.

[11] Patent Number: 5,224,940
[45] Date of Patent: Jul. 6, 1993

[54] DEVICE AND METHOD FOR PROTECTING HEALTH PERSONNEL FROM BODY FLUID BACKSPLASH

[76] Inventors: Chandler R. Dann, 4432 Paul Ct.; Chandler R. Dann, 2750 Christian Valley Rd., both of Auburn, Calif. 95603

[21] Appl. No.: 892,115

[22] Filed: Jun. 2, 1992

Related U.S. Application Data

[63] Continuation-in-part of Ser. No. 826,817, Jan. 29, 1992.

[51] Int. Cl.[5] .................................. A61M 35/00
[52] U.S. Cl. .................................. 604/290; 604/311; 604/187
[58] Field of Search ............ 604/73, 289, 290, 305, 604/310, 311, 187; 128/837, 841, 839

[56] References Cited

U.S. PATENT DOCUMENTS

| | | |
|---|---|---|
| 452,131 | 5/1891 | Haughawout . |
| 517,274 | 3/1894 | Gollings . |
| 3,026,874 | 3/1962 | Stevens . |
| 3,288,140 | 11/1966 | McCarthy . |
| 3,367,332 | 2/1968 | Groves . |
| 4,553,967 | 11/1985 | Ferguson et al. . |
| 4,769,003 | 6/1988 | Stamler . |
| 4,798,599 | 1/1989 | Thomas . |
| 4,898,588 | 2/1990 | Roberts ............... 604/187 |
| 4,911,688 | 2/1990 | Jones . |

FOREIGN PATENT DOCUMENTS

| | | |
|---|---|---|
| 2809828 | 9/1978 | Fed. Rep. of Germany . |
| 641061 | 8/1950 | United Kingdom . |

OTHER PUBLICATIONS

ZeroWet, Inc., Promotional Material, Nov. 1, 1991.

Primary Examiner—Randy C. Shay
Attorney, Agent, or Firm—Oliff & Berridge

[57] ABSTRACT

A splash shield for containing contaminated fluids from a wound and a method of use are disclosed. The shield is a transparent dome-shaped body made from a plastic film. The shield can be pierced by a sharp medical instrument, such as a hypodermic syringe or scalpel, and the wound cleansing or draining operation takes place under the shield as it is held against the patient. The shield is deformed by hand to conform to the wound site. The shield can also be hand held above and spaced from the wound site while the cleansing or draining operation takes place, to intercept and provide protection from splashed or squirted fluids. The shield is provided in single use, disposable form.

29 Claims, 4 Drawing Sheets

DEVICE AND METHOD FOR PROTECTING HEALTH PERSONNEL FROM BODY FLUID BACKSPLASH

RELATED APPLICATION

This application is a continuation-in-part of application Ser. No. 07/826,817 filed Jan. 29, 1992.

BACKGROUND OF THE INVENTION

1. Field of the Invention

This invention relates to the protection of health care personnel from potentially contaminated fluids. In particular, it relates to a shield and method of using a shield for containing spent irrigation fluids or wound drainage fluids.

2. Related Developments

Heretofore, body fluids resulting from procedures such as wound irrigation and abscess-drainage frequently splashed or squirted back onto the physician or health care personnel performing the procedure. This is highly undesirable, especially if the irrigation fluid or wound abscess fluid are contaminated by Human Immunodeficiency Virus, hepatitis Type B or C viruses, or other pathogens capable of transmitting disease by contact with mucous membranes or openings in the skin. Thus, these fluids present infectious hazards to health care personnel and can also soil clothing. The common practice has been to use several gauze pads to partially block the spray of body fluids, such as blood or purulent material, while allowing a compromised view of the task at hand. While offering some protection to the operator, the degree of protection is unfortunately inversely proportional to the operator's ability to see the wound site. Other methods to cope with this problem have included protective face shields, goggles or stationary plastic sheeting erected between the operator and his patient. The various goggles and face shields have ceased to gain wide acceptance and use due to discomfort, cost, and a need for cleaning between use. Goggles and face shields also do nothing to protect the clothing of both the operator and the patient. The plastic sheet barriers also require cleaning or a change of the sheet, lack mobility, and do not prevent the splash of body fluids onto the patient, linens, and forearms of the operator. The "Simpulse Pulsed Lavage System" marketed by Davol Inc. is a self-contained, high volume, high velocity wound irrigation system designed to prevent contamination of the patient and health care personnel in the irrigation fluid. However, this system is limited to use in the operating room due to its size, cost, and the production of one or more liters of blood-tinged saline.

U.S. Pat. No. 4,769,003 shows a splash shield for preventing backsplash of irrigation fluid. In this device, a syringe body is affixed to a central irrigation port that is spaced a substantial distance from the wound site. In addition, this shield is quite rigid and cannot be pierced by medical instruments, such as hypodermic syringes or scalpels, and cannot be easily conformed by hand applied force to the shape of the wound site.

U.S. Pat. No. 3,367,332 and U.S. Pat. No. 4,911,688 show sealing devices placed over a wound to enhance cleansing, healing or disinfection with irrigation fluids. These arrangements show insertion of hypodermic needles into membranes communicating or forming fluid filled chambers. However, these designs do not show hand-held shields for preventing backsplash.

German Printed Patent Publication No. 28 09 828 also illustrates a protective cover for irrigating wounds, which cover is adhesively fixed to a body.

British Patent No. 641,061 shows an irrigation system with a wound cover strapped in place over the wound.

U.S. Pat. No. 4,798,599 shows an eye cup with an irrigation fluid supply and collection system.

SUMMARY OF THE INVENTION

It is an object of the invention to provide a low cost, hand-held device and method of using the device for protecting health care workers from the spray or splash of irrigation or body fluids.

It is another object of the invention to provide a low cost shield through which wound treatment procedures can take place by piercing the wall of the shield to allow optimum positioning of medical instruments; it is a further object of the invention to provide a hand-held shield capable of being conformed to the wound site; it is a further object of the invention to provide a single use, low cost, sterile device and method for its use for maximizing the protection of health care personnel from infectious disease while performing medical procedures.

Briefly, these and other objects of the invention are achieved by the use of a transparent dome-shaped shield that can be placed near or over the wound site to contain splashing or squirting of irrigation or wound fluids. The wall of the shield has sufficient rigidity to maintain the dome-shape of the shield but is pierceable by medical instruments for performing medical procedures at a wound site covered by the shield. The shield can be manually conformed to the shape of the wound site to maximize splash protection. The shield can be provided as a sterile, single use product.

DESCRIPTION OF PREFERRED EMBODIMENTS

This invention relates to a pliable, clear, pierceable, hand-held dome-shape shield and to methods of using such a shield to contain backsplash of contaminated fluids during medical procedures.

Figure 2:
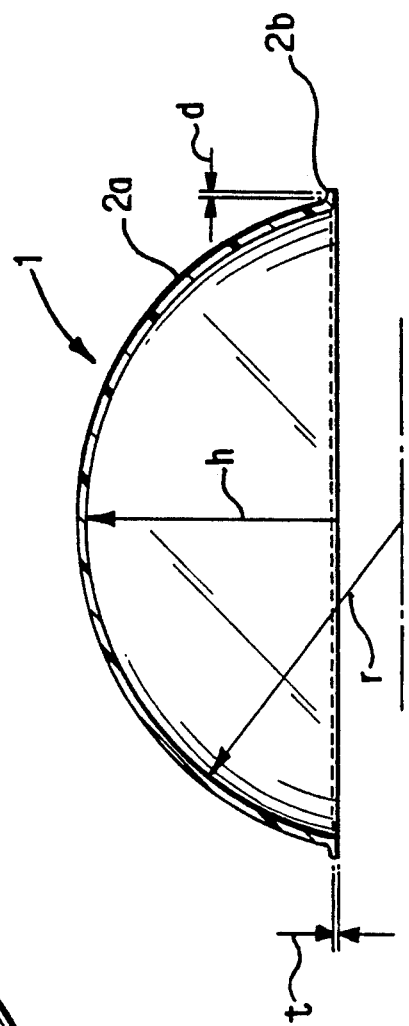
FIG. 2 is a cross-section of the shield taken along line II—II of FIG. 1.
Figure 1:
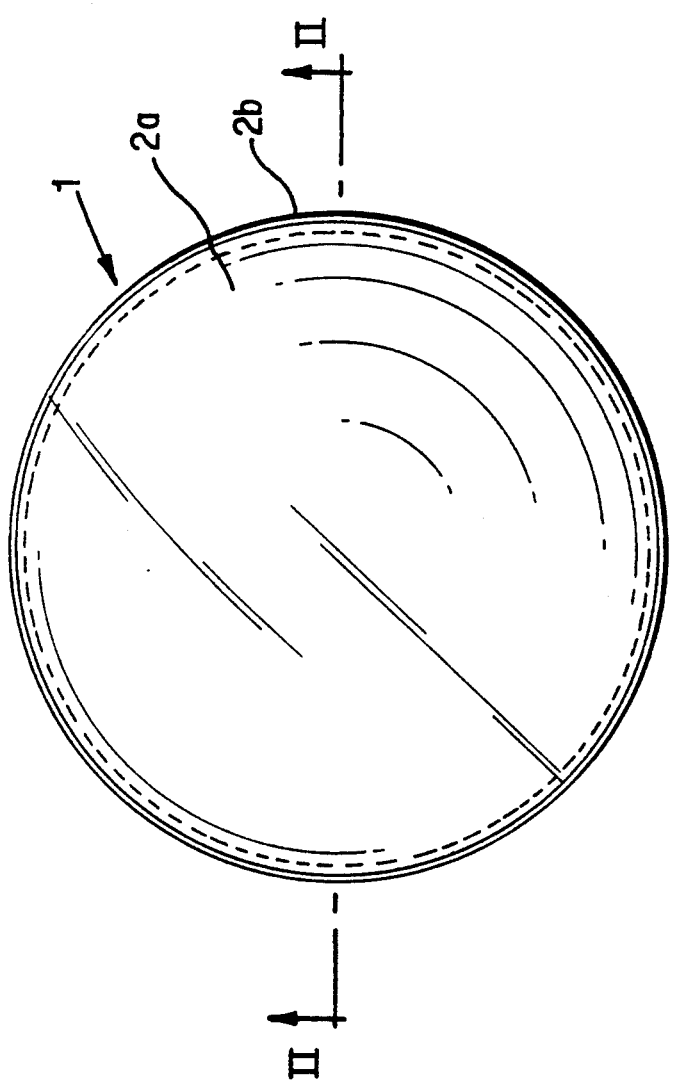
FIG. 1 is a top view of a shield embodying the invention.

A suitable shield embodying features of the invention is shown in FIGS. 1 and 2. The shield 1 comprises a dome-shaped body 2a having a small, out-turned flange or rim 2b. The shield 1 is formed of a substantially transparent plastic sheet material that is sufficiently rigid to form a stable, self sustaining dome-shape, yet is capable of being pierced by sharp medical instruments, such as hypodermic needles and scalpels. The body 2a of the shield 1 can be formed in substantially any dome-shaped configuration, with a preferred shape being that of a truncated hemisphere, as shown in FIG. 2. The body 2a is of a size to be readily hand-held and manipulable. The radius r can be from about 1.5 to about 3 inches. A shield in the form of a truncated hemisphere having a radius r of about 1.75 inches and a height h of about 1.3 inches has been found to be particularly useful in the present invention.

Preferably, the shield body 2a and flange 2b are integrally formed from a clear or transparent synthetic polymeric material, so that the wound site can be seen through the shield body 1. The material forming the shield provides a relatively rigid body 2a capable of maintaining the dome-shape, yet being sufficiently thin to allow the shield 1 to be pierced by medical instruments, such as hypodermic syringes and scalpels. One material that has been found particularly useful for this purpose is a thermoplastic plastic polyester sold under the tradename PETG by Eastman Kodak Corporation. Such sheet material having a thickness t of about 0.012 to about 0.02 inches has been found particularly useful for this purpose. Such a material can be shaped by conventional methods, such as thermoforming, to form the shield 1. It is desirable to form the shield 1 of materials that can be subjected to industrial sterilization processes, such as gaseous ethylene oxide or irradiation processes. If radiation sterilization is contemplated, the material forming the shield 1 should be radiation stable. Also, other transparent rigid, thermoplastic films made from materials such as polyvinyl chloride, can be used to form the shield 1.

The rim 2b is provided for comfortable contact with the skin of the patient and to provide resistance to collapse of the body 2a upon application of inwardly directed forces applied to opposed sides of the body 2a. An aspect of the flange width d is that it be sufficient to provide some peripheral stabilization of the shape of the shield yet not interfere with the ability to conform the shield to the wound site by application of opposed, laterally directed forces hand applied to the dome-shaped body 2a. Consequently, the rim 2b is relatively narrow. For example, with a hemispherical shaped shield having the dimensions discussed above, a flange width of approximately 0.06 inches is useful. Because the shield is used as a temporary barrier, the lower surface of the rim 2b can be free of adhesives for adhering the shield 1 to the skin of the patient.

Figure 3A:
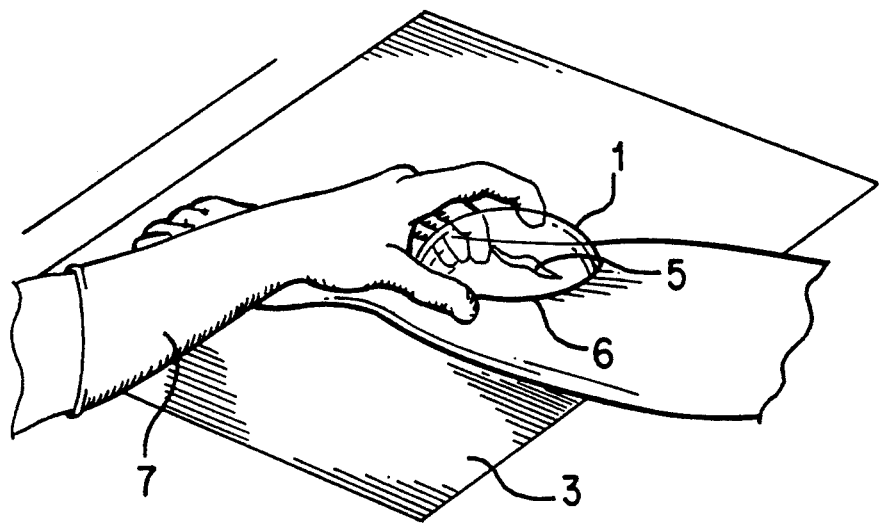
FIG. 3A shows the shield of FIG. 1 placed on a patient's skin and conforming to the general contour of the body part.
Figure 3B:
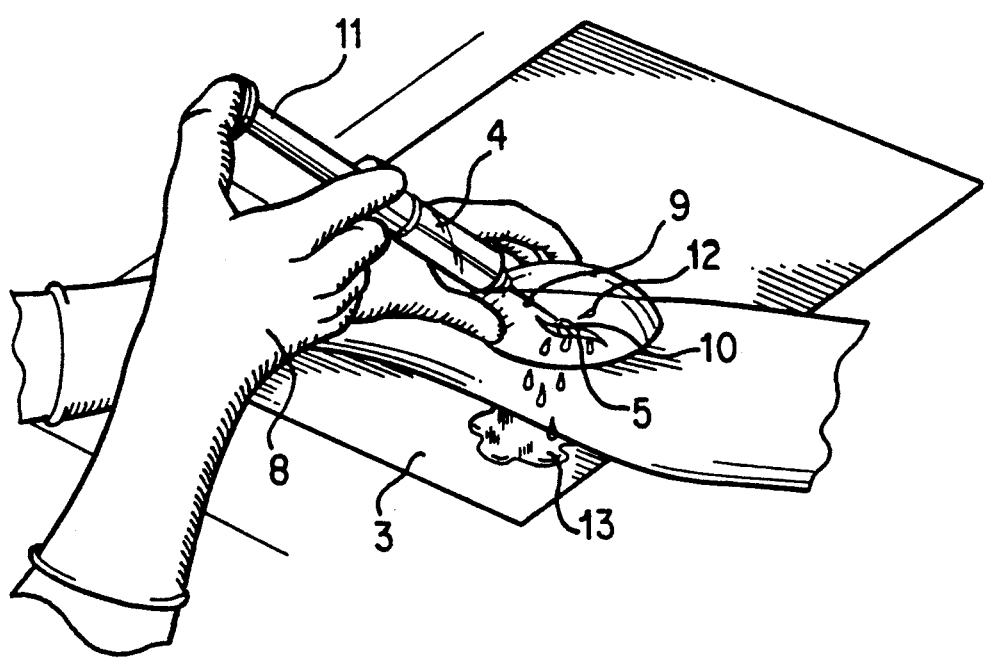
FIG. 3B shows the shield as positioned in FIG. 3A pierced by a needled irrigating hypodermic syringe and enclosing backsplash produced by wound irrigation.

One method of use of shield 1 as shown in FIG. 3A involves the following steps. An absorbent cloth or disposable pad 3 is placed under the body part with the wound 5 to be irrigated. The sterile plastic shield 1 is taken from the sterile instrument tray with the fingers gripping either side near the outer edges. The shield 1 is placed over the wound 5 with the rim 2b against the skin 6. The operator then conforms the flexible clear plastic shield 1 by squeezing the sides with one hand 7 as necessary to get the best seal with the underlying skin forming the wound margins, as shown in FIG. 3A. A needled hypodermic syringe 4 containing sterile saline or other irrigating fluid is manipulated with the operator's other hand 8 to pierce the dome-shaped body 2a of the shield at 9 over the underlying wound 5, as shown in FIG. 3B. Alternately, the shield 1 may be pierced by the syringe before the shield is placed on the patient. Irrigation of the wound with a stream of fluid 10 is accomplished in the traditional fashion by applying pressure to the syringe plunger 11, forcing a stream of fluid 10 from the needle into the wound 5, thereby dislodging foreign materials and blood clots and cleansing the tissues of microbial, chemical or other contaminants. Adherent foreign material in the wound 5 may be dislodged by the needle tip. The transparent plastic shield 1 allows direct visualization of the procedure while preventing the backsplash 12 of blood-tinged fluid onto the operator or surrounding linens. Of special concern is the prevention of this spray from contacting the mucous membranes of the operator's eyes, nose and mouth, which could cause transmission of various diseases such as Human Immunodeficiency Virus or serum hepatitis (Type B or C). The effluent irrigation fluid is allowed to coalesce and form droplets 13 that flow down onto the absorbent pad 3 placed earlier beneath the patient. The absorbent pad 3 is discarded at the end of the procedure, according to prevailing medical practice. If the wound dimensions are larger than the shield, irrigation is accomplished by serial placement of the shield until the wound is entirely cleansed.

Figure 3C:
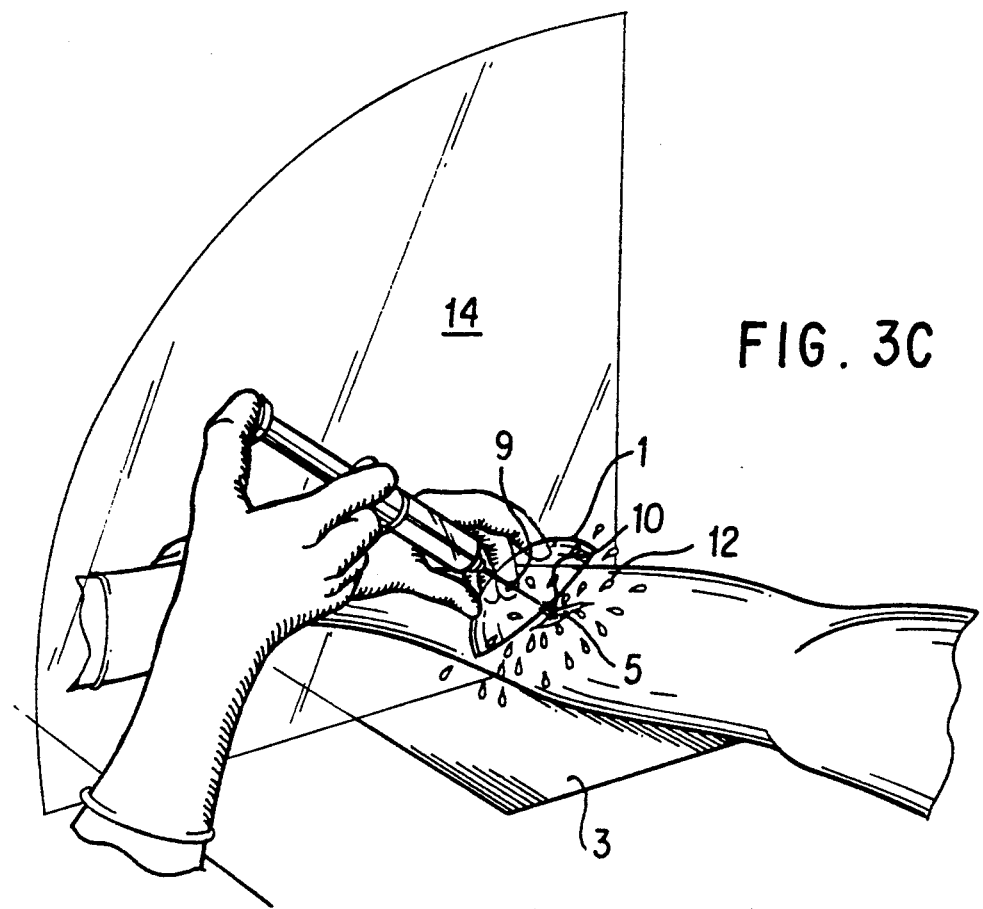
FIG. 3C shows the shield of FIG. pierced with a needled irrigating syringe but held out of contact with the wound margins and providing a shield from contaminated backsplash.

Some areas of the body may not allow desired conformation of the shield to the skin surface, as depicted in FIG. 3C. In this situation the shield 1 still provides substantial protection to the health care worker by creating a splash-free zone 14 substantially in the shape of a solid sector of a sphere. This procedure is the same as outlined for FIG. 3B except no attempt is made to conform the plastic shield to the skin surface. The shield 1 is pierced by the irrigating needle 9 but remains above the surface of the skin. It is held in position on the shaft of the needle by either friction with the plastic or with one of the operator's hands. When irrigation fluid 10 is forced into the wound, backsplash 12 is produced but blocked in its path toward the operator by the clear plastic shield 1, providing substantial protection while allowing direct line of sight for the operator. Since the degree of backsplash reduction is inversely proportional to the distance between the dome and the wound being irrigated, it is desirable to keep the dome 1 and syringe 4 as close to the wound 5 as possible. At the end of the procedure, all single use items and the absorbent pad(s) 3 are disposed of in the locally prescribed fashion.

Figure 3D:
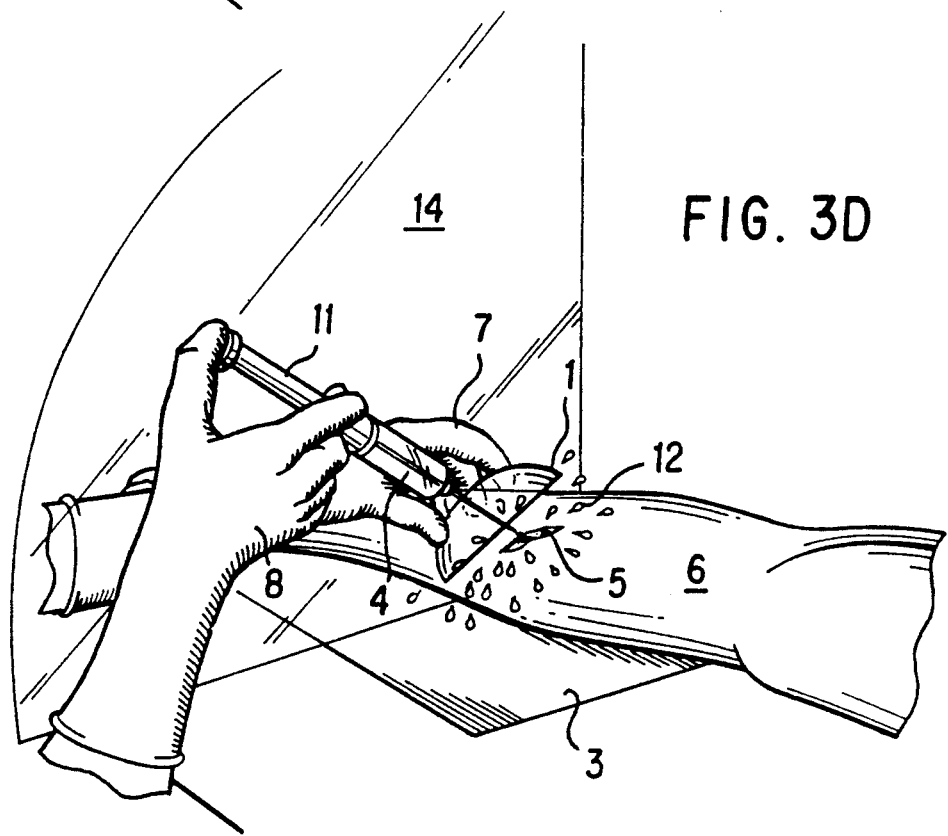
FIG. 3D shows the shield of FIG. 1 held slightly above a wound site while a needled irrigation syringe is passed under the shield, with the shield providing protection against backsplash.

Alternatively, the shield 1 can also be used as shown in FIG. 3D, without piercing by a medical instrument. The shield is held by the non-dominant hand 7 of the user near the wound site, a sufficient distance, usually 1 to 2 inches, to allow an instrument, such as an irrigation syringe 4, to be manipulated adjacent the wound. The shield 1 is positioned to prevent backsplash toward the user and provides a zone of splash protection 14 in the form of a sector of a sphere, as in the method of use described with respect to FIG. 3C. Fluid droplets coalesce within the interior of the shield and fall, as larger drops, onto an absorbent cloth 3 placed adjacent or under the part of the body where the wound is situated. As with previously described methods of use, the wound site can be visualized through the shield while the wound treatment is taking place.

Figure 4:
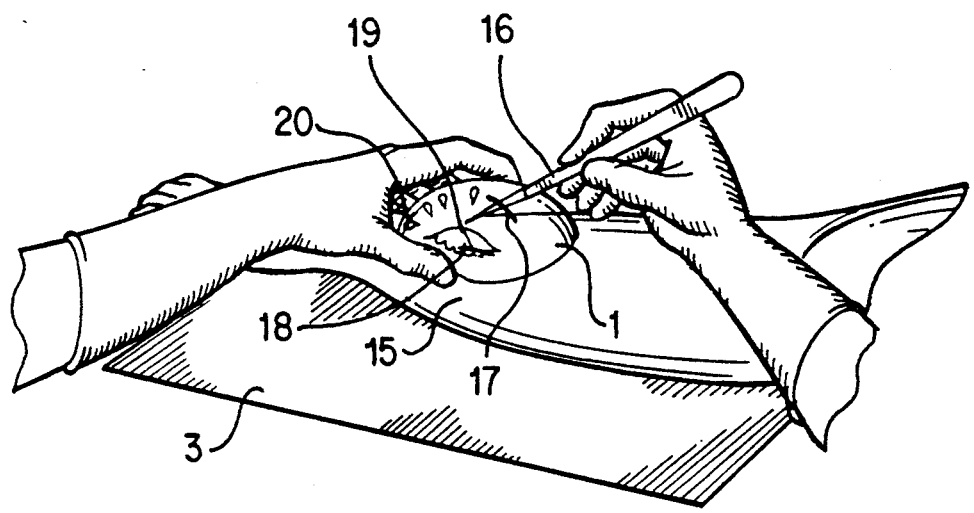
FIG. 4 shows the shield of FIG. 1 being pierced with a scalpel during incision and drainage of an abscess, thereby preventing expulsion of purulent material onto health care personnel.

Other methods of use for this type of device include the incision and drainage of body fluid cavities which may be under pressure. In FIG. 4 the procedure is much the same as outlined for wound irrigation in FIG. 3A including placement of absorbent pad(s) 3 under the affected body part 15. Instead of using a hypodermic syringe and needle, a scalpel 16 or other penetrating device is used to pierce the plastic shield 1 which has been placed over an abscess, hematoma or other subcutaneous fluid cavity 18 potentially under pressure. The fluid cavity 18 may be incised with an incision 19 and drained below the protective barrier provided by the shield. Once the fluid 20 under pressure is initially released, the shield may be removed and properly discarded. This method of use protects the operator from expelled purulent or other body fluids 20, which could potentially transmit disease. Alternatively, the shield 1 may be held a short distance from the incision site, similar to the manner as described with respect to FIG. 3D. The shield is held by the user in a position to intercept splashing or squirting fluid from the incision.

Figure 5:
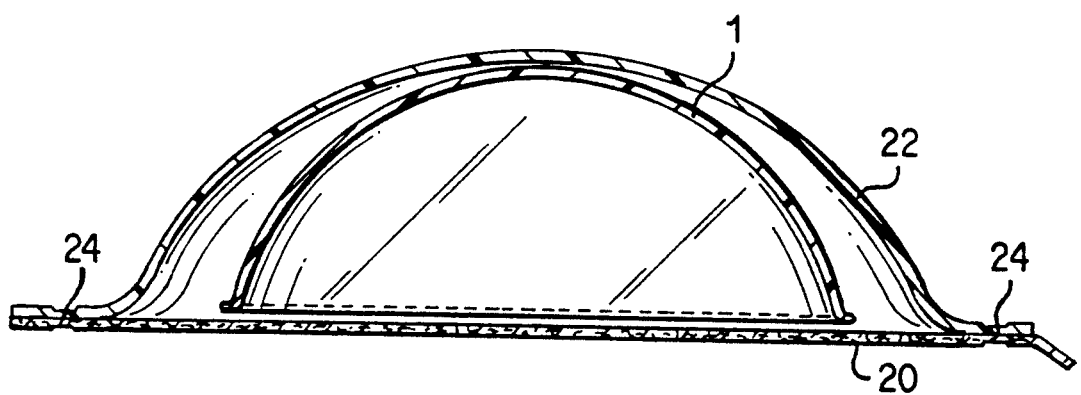
FIG. 5 is a cross-section view of the shield shown in FIG. 1 contained in a sterility barrier package.

Preferably, the shield 1 is provided in a sterile, single use, disposable form. Referring to FIG. 5, the dome 1 is contained within a sterility barrier package formed by the lower sheet 20 and the upper sheet 22 that are joined together by suitable means, such as a peripheral heat seal 24. The sheets 20 and 22 are formed of medical packaging materials that form a microbe impervious barrier so that, once the packaged shield 1 is sterilized, it is maintained in sterile condition within the enclosure formed by the films 20 and 22. Suitable packaging materials are known to those in the medical device art and the choice of such materials depends largely on the type of sterilization system used, either gas or irradiation. Ideally, the films 20 and 22 are joined in a manner such that they can be readily peeled apart to allow sterile delivery of the shield 1 to the operating field.

As can be seen from the foregoing discussion, a device and method are disclosed that provide significant advantages. A sealed enclosure having high fluid integrity can be provided at a low cost. The wound site is highly visible and the pierceable shield allows optimal placement of medical instruments with respect to the wound. The shield is useful for both irrigation purposes and for performing fluid drainage operations. The shield may be used alternatively in a pierced or non-pierced mode, depending on the physicians preference or the exigencies of the procedure. The use of the shield encourages aggressive irrigation, thereby promoting thorough wound cleaning and reducing wound infections.

We claim:

1. A shield for containing fluid splashed from a wound site comprising:
    a hollow, transparent, form-stable, hand holdable, imperforate dome-shaped body having a wall, said wall comprising means for enabling piercing of the wall over a substantial portion thereof by hand manipulated medical instruments, and
    a peripheral rim extending outwardly of the dome-shaped body.

2. A shield as in claim 1, wherein the body is formed of a thermoplastic material.

3. A shield as in claim 2, wherein the thermoplastic material is a polymeric sheet material having a thickness of about 0.012 to about 0.020 inches.

4. A shield as in claim 3, wherein the sheet material is a polyester.

5. A shield as in claim 4, wherein the polyester is a radiation stabilized polyester.

6. A shield as in claim 1, wherein the dome-shaped body is a truncated hemisphere.

7. A shield as in claim 1, wherein the rim is free of an adhesive for adhering the body to the wound site.

8. A shield as in claim 1, and further comprising:
    a sterility barrier package surrounding the shield, the shield being maintained in a sterile condition within the package.

9. A shield for containing fluid from a wound site consisting essential of:
    a hollow, transparent, form-stable, hand holdable imperforate dome-shaped body having a wall, said wall comprising means for enabling piercing of the wall over a substantial portion thereof by hand manipulated medical instruments, and
    a peripheral rim extending outwardly of the dome-shaped body.

10. The shield as in claim 9, wherein the dome-shaped body is formed of a thermoplastic film material having a thickness of about 0.012 to about 0.02 inches.

11. The shield as in claim 10, wherein the film material is a thermoplastic polyester.

12. The shield as in claim 9, wherein the dome-shaped body is hemispherical.

13. The shield as in claim 9 wherein the dome-shaped body is a truncated hemisphere having a radius of about 1.75 inches and a height of about 1.3 inches.

14. A method of irrigating a wound comprising the steps of:
    placing a hollow, substantially transparent, imperforate dome-shaped shield adjacent the wound site, said shield having a wall comprising means for enabling piercing of the wall over a substantial portion thereof;
    piercing the wall of the shield with a hypodermic syringe containing an irrigation fluid; and
    directing a stream of irrigating fluid from the hypodermic syringe at the wound.

15. A method as in claim 14, further comprising the step of maintaining the shield over the wound site while the stream of irrigation fluid is directed at the wound.

16. A method as in claim 15, wherein the step of maintaining the shield over the wound site comprises manually holding peripheral edges of the shield in engagement with margins of the wound site.

17. A method as in claim 16, further comprising the step of manually applying a laterally directed force to the wall of the shield to conform the shield to the wound site.

18. A method as in claim 14 and further comprising the step of collecting spent irrigation fluid from the wound site.

19. A method as in claim 18, wherein the step of collecting spent irrigation fluid comprises absorbing the spent fluid in an absorbent member located to receive spent irrigation fluid flowing from the wound site.

20. A method for containing the flow of fluids from a wound site comprising the steps of:
    placing a hollow, substantially transparent imperforate dome-shaped shield over the wound site, said shield having a wall comprising means for enabling piercing of the wall over a substantial portion thereof;
    piercing the wall of the shield to form an opening;

treating the wound site with a medical instrument inserted through the opening formed in the wall of the shield; and maintaining the shield over the wound site while the wound is being treated to limit the projection of fluids from the wound site.

21. A method as in claim 20, wherein the step of maintaining the shield over the wound site further comprising holding an edge of the shield in contact with tissue at a margin of the wound site.

22. A method as in claim 21, wherein the step of maintaining the shield over the wound site comprises manually holding the shield in place.

23. A method as in claim 21, and further comprising the step of manually applying a lateral force to the shield to conform the shape of the shield while the shield is manually held in place, to conform the shape of the shield to the wound site.

24. A method as in claim 20, wherein the step of piercing the shield is accomplished by the medical instrument used in treating the wound site.

25. A method of treating a wound comprising:

holding a conformable, transparent, imperforate dome-shaped shield adjacent a wound site with a first hand of a user, said shield having a wall comprising means for enabling piercing of the wall over a substantial portion thereof; and with a second hand of the user carrying out a wound treatment at the wound site; and maintaining the shield adjacent the wound site with said first hand as the wound treatment procedure is carried out to prevent liquids from the wound site from travelling toward the user.

26. A method as in claim 25, wherein the shield is conformed to the shape of the wound site by the first hand of the user during the wound treatment procedure.

27. A method as in claim 25, wherein the shield is held in spaced relation to the wound site and the wound treatment procedure is conducted beneath the shield.

28. A method as in claim 27, wherein the wound treatment procedure is irrigation.

29. A method as in claim 27, wherein the wound treatment procedure is drainage.

* * * * *